United States Patent [19]

Rossen

[11] Patent Number: 4,989,605
[45] Date of Patent: Feb. 5, 1991

[54] TRANSCUTANEOUS ELECTRICAL NERVE STIMULATION (TENS) DEVICE

[76] Inventor: Joel Rossen, 604 Sartori Dr., Petaluma, Calif. 94952

[21] Appl. No.: 331,181

[22] Filed: Mar. 31, 1989

[51] Int. Cl.⁵ .............................................. A61N 1/34
[52] U.S. Cl. .................................. 128/422; 128/421; 128/907
[58] Field of Search ........... 128/421, 422, 423, 419 R, 128/639, 783, 907, 395, 735, 423 W

[56] References Cited

U.S. PATENT DOCUMENTS

| 3,785,383 | 1/1974 | Dotto | 128/414 |
|---|---|---|---|
| 3,902,502 | 9/1975 | Liss et al. | 128/422 |
| 4,019,510 | 4/1977 | Ellis | 128/421 |
| 4,112,923 | 9/1978 | Tomecek | 128/735 |
| 4,177,819 | 12/1979 | Kofsky et al. | 128/422 |
| 4,232,678 | 11/1980 | Skovajsa | 128/395 |
| 4,232,680 | 11/1980 | Hudleson et al. | 128/422 |
| 4,338,945 | 7/1982 | Kosugi et al. | 128/421 |
| 4,535,777 | 8/1985 | Castel | 128/421 |
| 4,535,784 | 8/1985 | Rohlicek et al. | 128/907 |
| 4,553,546 | 11/1985 | Javelle | 128/395 |
| 4,646,743 | 3/1987 | Parris | 128/396 |
| 4,719,922 | 1/1988 | Padjen et al. | 128/421 |
| 4,844,075 | 7/1989 | Liss et al. | 128/421 |
| 4,856,526 | 8/1989 | Liss et al. | 128/422 |

FOREIGN PATENT DOCUMENTS

| 0058105 | 2/1981 | European Pat. Off. | 128/907 |
|---|---|---|---|
| 2371935 | 7/1978 | France . | |

Primary Examiner—Lee S. Cohen
Assistant Examiner—Kennedy J. Schaetzle

[57] ABSTRACT

An improved transcutaneous electrical nerve stimulator (TENS) involving a microcurrent (typically 25 to 900 microamps) monophase D.C. carrier signal (typically 10,000 to 19,000 Hz, preferably 15,000 Hz) that is modulated on and off in time (typically at 0.3 Hz up to 10,000 Hz, preferably 9.125 Hz followed by 292 Hz) and further inverted about every second by reversing the polarity of the signal at the electrodes. Such a device has been found to be useful in alleviating pain very rapidly.

15 Claims, 7 Drawing Sheets 4,989,605

TRANSCUTANEOUS ELECTRICAL NERVE STIMULATION (TENS) DEVICE

BACKGROUND OF THE INVENTION

1. Field of the Invention

This invention relates to an improved transcutaneous electrical nerve stimulation (TENS) apparatus for symptomatic relief and management of chronic (long term) intractable pain and adjunctive treatment in the management of postsurgical traumatic acute pain. More specifically, the invention relates to a TENS device that operates in the electrical current range of about 25 microamps to less than 1 milliamp using a chopped (e.g., 9.125 Hz or 292 Hz) carrier frequency (e.g., 15,000 Hz) having typically a monophasic wave profile which is preferably inverted (reversed polarity) approximately every second.

2. Description of the Prior Art

It is generally known and an accepted practice to administer transcutaneous energy in the form of light and/or electrical current as a therapeutic treatment particularly to alleviate certain types of pain. Such treatments are frequently compared to acupuncture both in terms of application and results. It is also generally known in both types of transcutaneous radiation therapy that the body will favorably respond to certain preselected discrete beat frequencies. Thus for example in U.S. Pat. No. 4,232,678; 4,553,546 and 4,646,743 and French patent No. 2371935 various types of infrared (IR) and/or near IR light sources are chopped (modulated on and off in time) at selected frequencies to produce a pulsating source of IR radiation as a transcutaneous energy to be applied to mammalian tissue. Analogously, U.S. Pat. Nos. 3,785,383 and 3,902,502 disclose a transcutaneously applied capacitively coupled electrostatic electrode system and a microcurrent conductivity coupled electrode system, respectively, for the purpose of reducing sensitivity to pain. In the later disclosure the concept of modulating the carrier frequency by superimposing a beat frequency is employed. Instruments specifically designed to accomplish this type of electric current therapy are now commonly referred to as transcutaneous electrical nerve stimulators (TENS).

SUMMARY OF THE INVENTION

The improved transcutaneous electrical nerve stimulator according to the present invention is categorically a microcurrent TENS which operates using a unique wave form. The instrument is constructed such that it will operate from about 25 microamps up to about 900 microamps current during therapeutic use with a peak current of the order of 6 milliamps. Typically the current is applied through a pair of electrodes in the form of a high frequency, monophasic, burst of a D.C. carrier signal (e.g., at lest 10,000 Hz to 19,000 Hz)that is chopped or modulated at a relatively lower frequency (e.g., from about 0.3 Hz up to 10,000 Hz). The burst of the modulated carrier signal are typically from about 0.05 seconds to about 10 seconds in duration with about one second in duration being preferred. Preferably, successive bursts are inverted relative to the previous burst by reversing the polarity at the electrodes thus simulating a biphasic wave form, yet the carrier is a monophasic D.C. signal. Preferably, the modulating frequency is selected from pairs of frequencies which exhibit specific therapeutic action (e.g., 292 Hz and 9.125 Hz). Advantageously the TENS can be performed synchronously with light stimulation and has been found to relieve pain extremely fast (typically in 1 to 3 minutes) under conditions that are below the level of human sensation.

Thus the present invention provides an improved transcutaneous electrical nerve stimulator comprising:

(a) a pair of electrode means for making surface contact and supplying electrical current to mammalian tissue; and (b) an electrical circuit means for supplying to the pair of electrode means from about 25 microamps up to about 900 microamps of a monophasic sequence of bursts of a D.C. carrier signal selected from the frequency range of at least 10,000 Hz to about 19,000 Hz which is modulated on and off in time at a frequency selected from the range of about 0.3 Hz up to 10,000 Hz and said bursts are characterized as having a periodicity greater in duration than that associated with the modulation frequency.

Preferably the microcurrent TENS device inverts the D.C. carrier signal between bursts by reversing the polarity at the pair of electrodes means. Most preferably this occurs about every second with the modulating frequency being selected from the group consisting of 9.125, 18.25, 73, 146, 292, 584, 168, 2336, and 4672 Hz with a D.C. carrier frequency of typically 15,000 Hz. For routine pain management the use of 9.125 Hz followed by 292 Hz is particularly useful. The present invention also provides a unique LED electrode that produces electromagnetic radiation synchronously with the electrical current therapy.

It is an object of the present invention to provide an improved TENS device that operates in the microcurrent range using a unique wave form. It is a further object to provide such a TENS device that exhibits enhanced ability to quickly manage pain. It is still a further object to provide such a TENS device that is highly compatible with other pain management therapies. Fulfillment of these objects and the presence and fulfillment of other objects will become apparent upon complete reading of the specification and claims taken in conjunction with the attached drawings.

DESCRIPTION OF THE PREFERRED EMBODIMENTS

Figure 1:
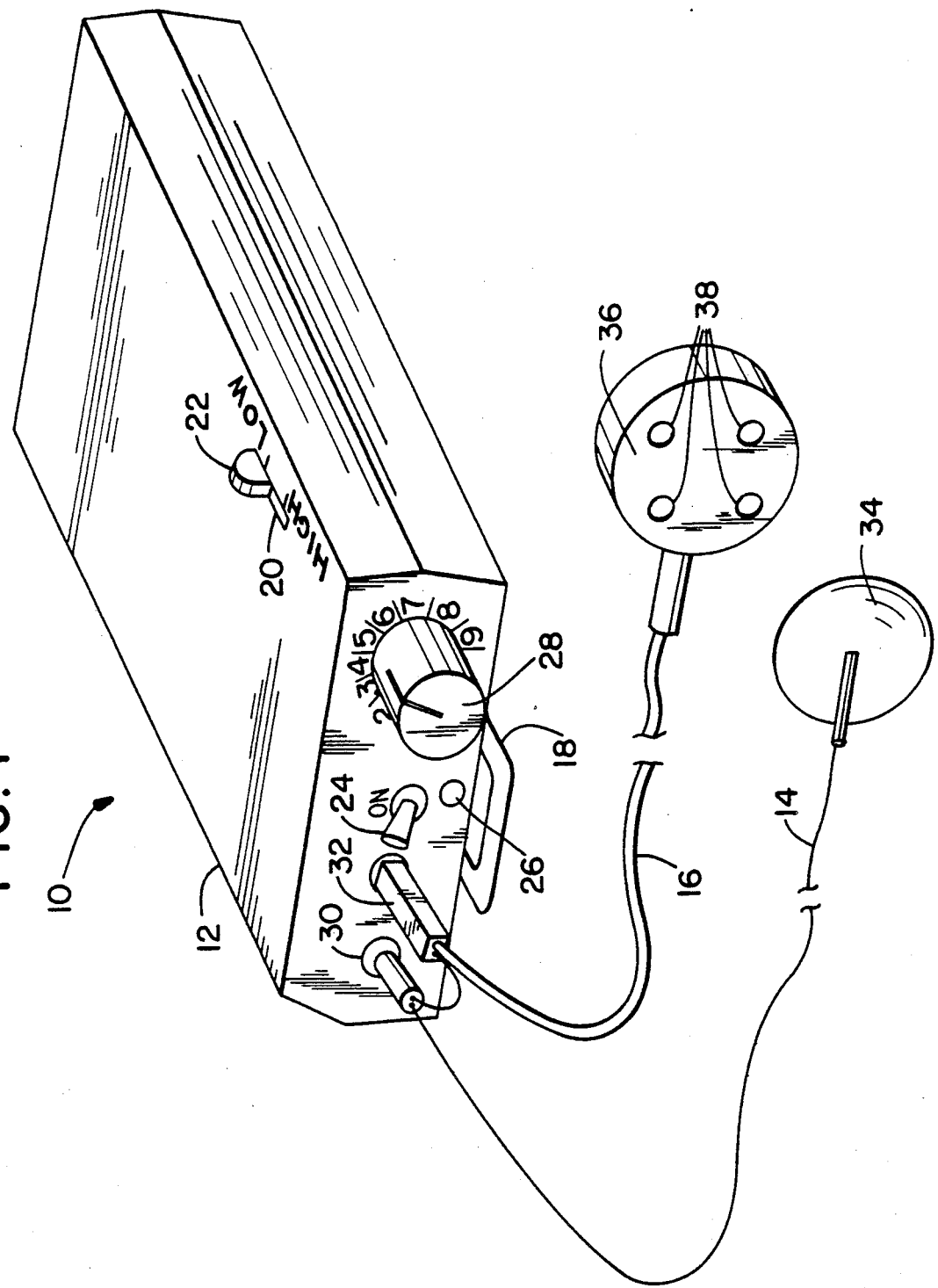
FIG. 1 is a perspective view of a transcutaneous electrical nerve stimulation apparatus according to the present invention.

The improved microcurrent transcutaneous electrical nerve stimulator according to the present invention, how it operates and how it is used, how it differs from previously known instruments and the advantages of using the improved device can perhaps be best explained and understood by reference to the drawings. FIG. 1 illustrates one particularly preferred embodiment of the present invention wherein the TENS unit (generally designated by the numeral 10) consists of a portable housing 12 with two external electrodes 14 and 16. In this particular embodiment the case or housing 12 is equipped with a clip 18 that allows the unit to be worn on the belt or the like during use. The other side of the case 12 relative to the belt clip 18 is equipped with a slot 20 that allows a sliding selector switch 22 to be used to set the beat frequency (i.e., the modulating frequency for turning the carrier signal on and off at a predetermined frequency characteristic of the therapeutic treatment being performed). In this particular illustrated embodiment only two frequency settings are available to the user (typically 9.125 Hz or 292 Hz). As such this particular embodiment is easily operated by the patient. In a more complex embodiment, a greater number of preselected discrete frequency settings are provided (for example, by making the slot 20 of the sliding selector switch 22 longer) thus producing a clinical or physician's version of the instrument.

The top face of the case 12 is further provided with an on/off switch 24 and a monitor light 26 along with an electrical current selector switch 28. Also there are two electrode connector terminals 30 and 32 provided on the top face of the case 12 which in this illustrated embodiment involve two separate types of energy emitting electrode systems. The first system involves two electrically conductive electrodes 34 and 36. Electrode 34 is a conventional self adhering neurostimulation electrode which is adhesively pressed to the skin or the like. The second current electrode 36 is a conductive pad that represents the outer skin contacting surface of both the second electrical current electrode and the light emitting diode (LED) system (the second type of energy emitting electrode system). As shown in FIG. 1, there is a set of four light emitting diodes 38 protruding through the current carrying electrode surface 36. Thus, in this particular embodiment, both the unique electrical wave form of the present invention and synchronous light radiation can be simultaneously applied transcutaneously at the same physical location. Typically this second electrode 36 is held adhesively to the skin or the like during use by the use of a transparent, conductive, double adhesive electrode patch (not shown).

The actual use of the TENS unit 10 illustrated in FIG. 1 is relatively simple and straightforward. The electrodes, typically either a pair of self adhering neurostimulation electrodes of approximately 32 millimeters in diameter such as supplied by Axelgaard Manufacturing Co. of Fallbrook, Calif., or one such electrode plus the specialized light/current electrode of FIG. 1 adhesively held by a 38.4 millimeter in diameter model 4×4sp electrode patch supplied by AcuData Software Medical Products Division of Petaluma, Calif., are positioned on mammalian skin tissue in accordance with a health care professional or physician's instructions. During use there are only two adjustments that need to be made. The current selector switch 28 on the top face of the housing 12 can be adjusted from 25 microamps up to a 6 milliamp peak output. The frequency selector 22 can be positioned wither high, e.g. 292 Hz, or low, e.g. 9.125 Hz. The on/off switch 24 when turned on will activate the on light 26 which flashes or blinks faster as the current setting is increased. As such, visual confirmation of the instrument being on and the particular current setting can be readily determined by looking at the light 26. During use the current can be adjusted by the user by use of switch 28. Typically the current is initially elevated until the perception of electrical stimulation is perceived. The current is then decreased until perception of stimulation is undetectable. Readjustment during treatment can be repeated as needed. Typically a setting of about three tenths of full scale for switch 28 represents an optimum effective setting.

One particularly preferred method of use for pain involving muscle spasms, tightness or chronic problems, starts with 9.125 Hz and the current turned up until it can be felt. The current setting is then lowered until the sensation is gone. The current is continuously lowered each time the sensation of stimulation becomes apparent until a setting is found where no further sensation appears for two minutes. The TENS unit is then switched to the high frequency setting. For acute pain such as post surgical pain or pain involving inflammation and/or swelling rather than muscle tightness or spasm, start with 292 Hz. Such procedures have been found to alleviate pain in as little as 1 to 3 minutes. Application of the TENS unit for periods in excess of twenty minutes is not generally needed although longer or even continual stimulation may be beneficial in selected cases.

Figure 2:
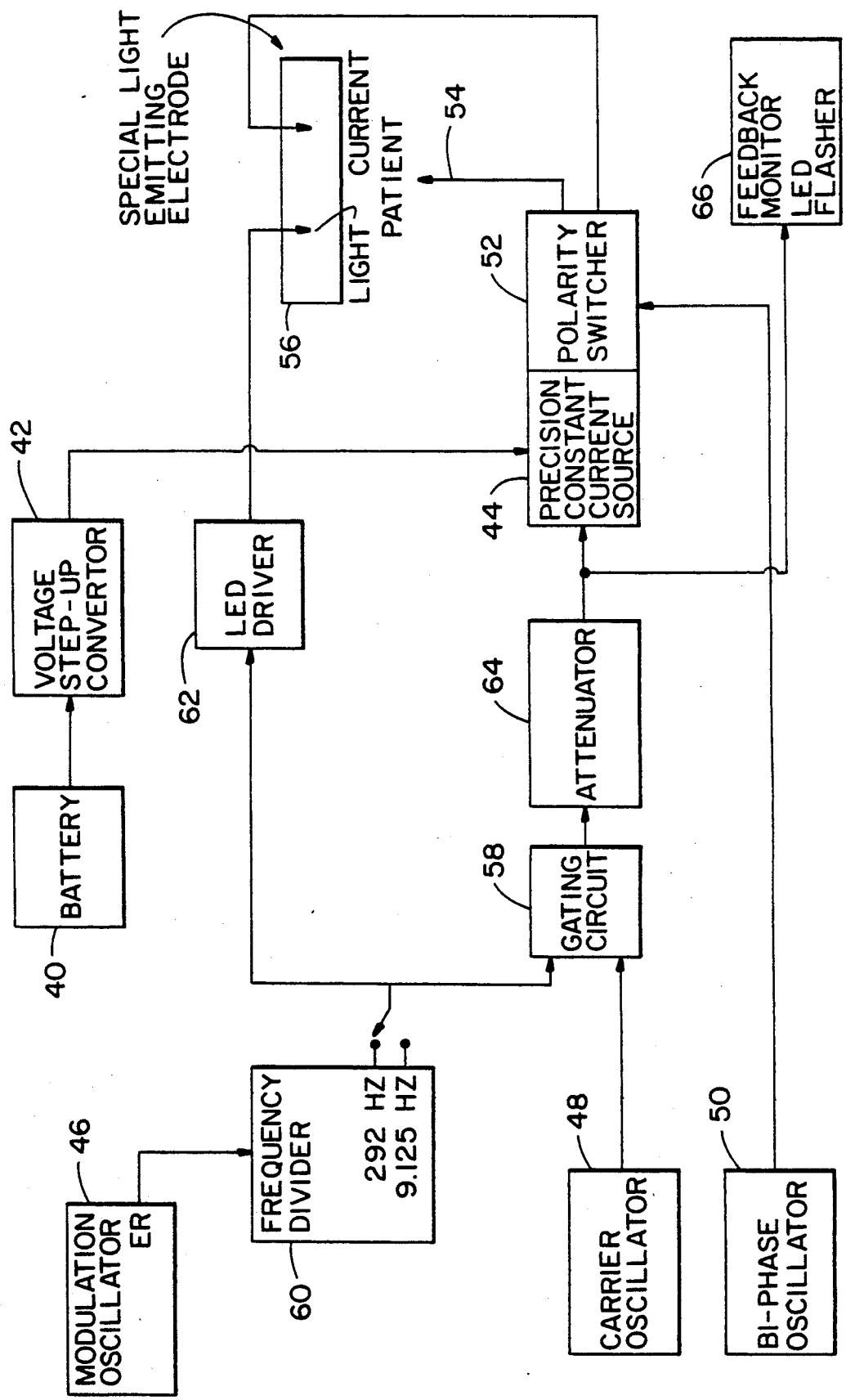
FIG. 2 is a block diagram illustrating the functional components making up a typical electrical circuit according to the present invention.

FIG. 2 is a block diagram of the individual components making up a typical electrical circuit for the embodiment of the TENS device shown in FIG. 1. The respective function of the individual components are indicated on the block diagram. As shown, the device is powered by a battery 40 supplying current to a voltage step-up converter 42. The voltage step-up converter typically produces a 30 volt source which is part of a precision constant current source 44 (for details see FIG. 2). The 30 volt is applied to the skin and a precision constant current sync regulates the current through the skin.

As further illustrated on the left side of FIG. 2, the electrical circuit involves a modulation oscillator 46, a carrier oscillator 48 and a bi-phase oscillator 50. The bi-phase oscillator 50 is typically a 0.05 second to 10 second oscillator that drives a polarity switcher 52 which in turn reverses the polarity of the current supplied by the precision constant current source 44 at the current electrodes 54 and 56. The carrier oscillator 48 is typically a 10,000 Hz to 19,000 Hz signal (preferably about 15,000 Hz) generator that drives one of the input sides of the gating circuit 58. The modulation oscillator 46 and frequency divider 60 are the source of the beat frequency that chops the carrier frequency on and off in time at preselected frequencies known to be beneficial for therapeutic purposes. As suggested in FIG. 2, the output from the frequency divider 60 is either 292 Hz or 9.125 Hz. This signal drives both the LED driver 62 and the other input side of the gating circuit 58. The LED driver 62 then drives the LED electrode 64 at the selected frequency synchronously with the current electrodes 54 and 56. The gating circuit 58 output is directed through attenuator 64 before the signal is directed to the precision constant current source 44 and polarity switcher 52. The output from the attenuator is also used to drive the feedback monitor LED flasher 66 thus alerting the patient that the TENS device is operating by flashing at a rate proportional to the current.

Figure 3A:
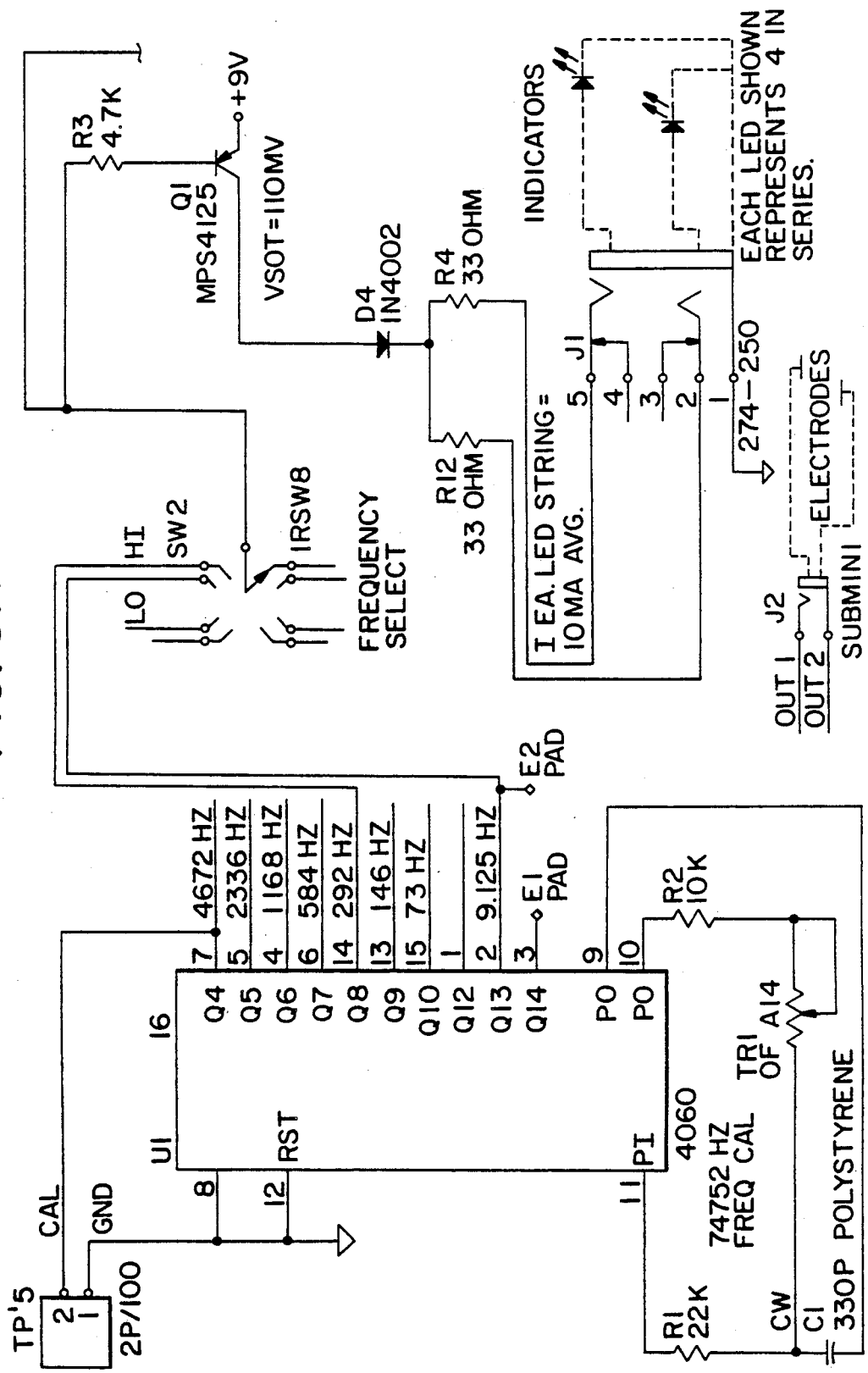
FIG. 3 is a detailed schematic of the electronic circuit of one preferred embodiment according to the present invention.
Figure 3A:
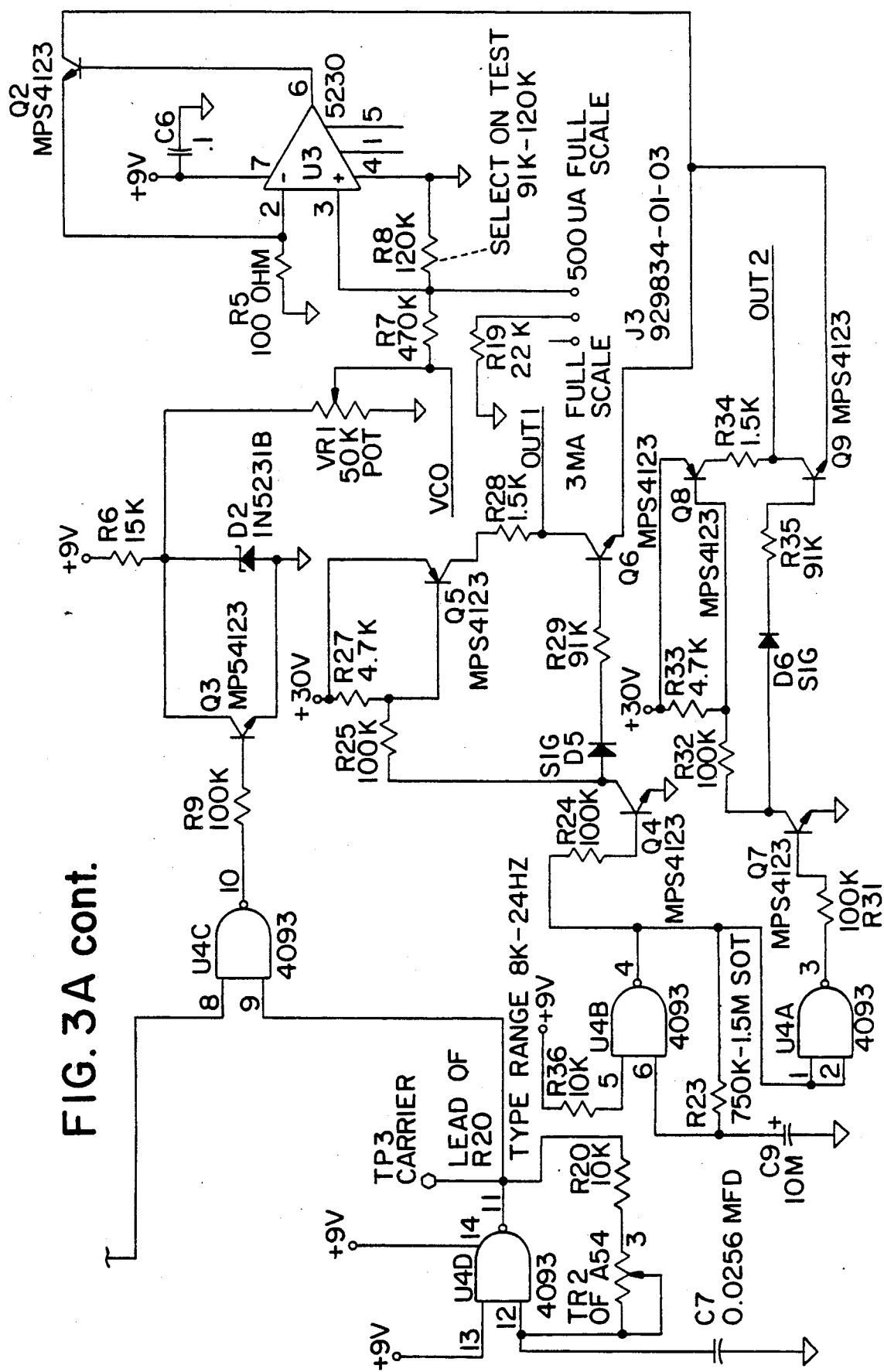
Figure 3B:
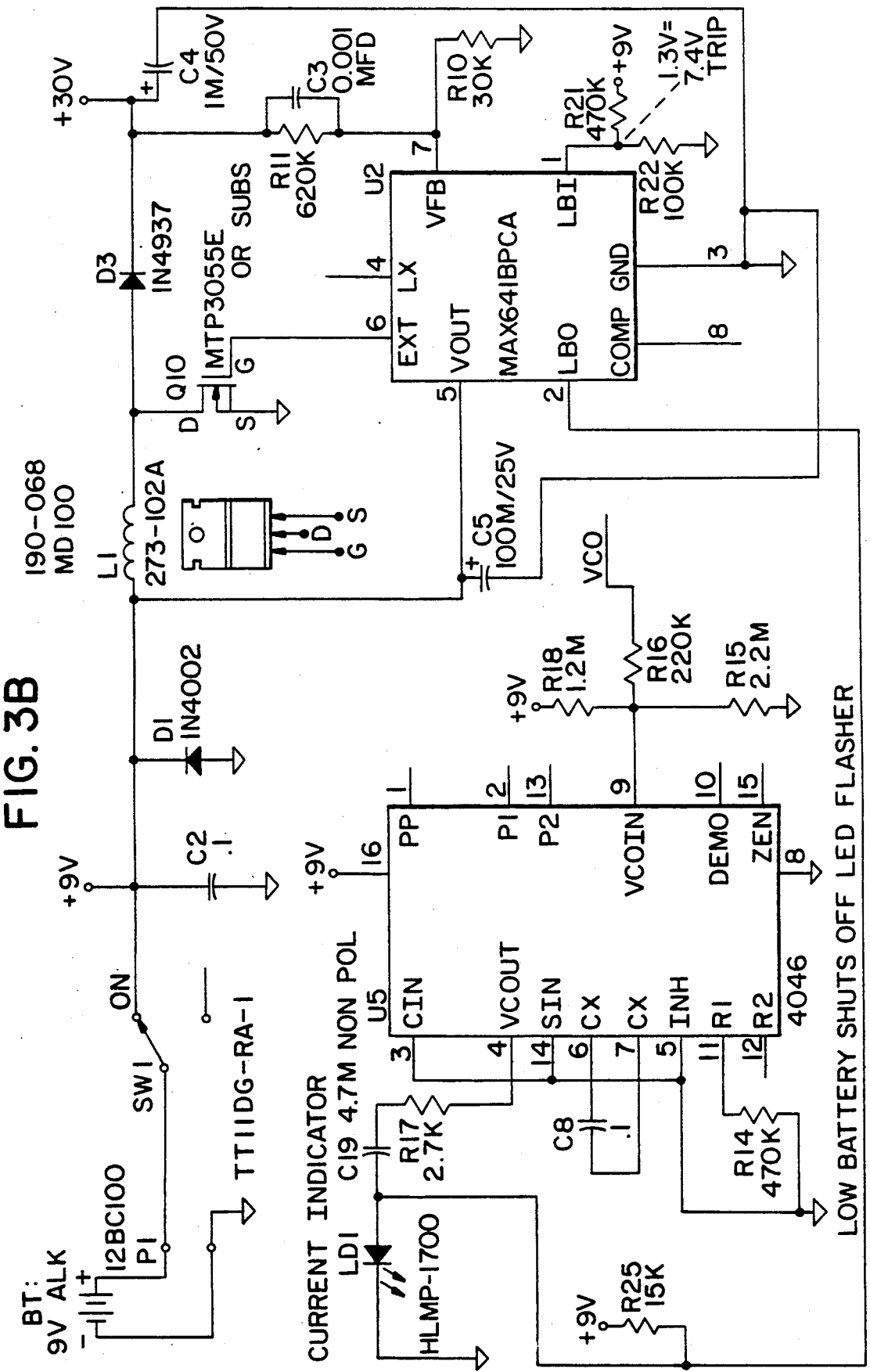

FIG. 3 is a detailed schematic of one preferred embodiment of the electrical circuitry according to the present invention. This particular circuitry is generic to both the 292 Hz/9.125 Hz modulated embodiment of FIGS. 1 and 2 as well as the physician's version having eight different selectable modulation frequencies. In presenting the schematic of FIG. 3, conventional electrical notation is employed to identify all components and relevant electrical component values. A single 9 volt portable radio type battery is employed as the current source. The following table of components categorizes and identifies the individual elements and associated circuitry corresponding to the functional block circuit description of FIG. 2.

TABLE

| (FIG. 2) | (FIG. 3) |
| --- | --- |
| Battery, 40 | BT1 9V Alk |
| Voltage Step-Up Converter, 42 | U2, Q10, L1 |
| Precision Constant Current Source 44 | U3, Q2 |
| Modulation Oscillator, 46 | U1 |
| Carrier Oscillator, 48 | U4D |
| Bi-Phase Oscillator, 50 | U4B |
| Polarity Switcher, 52 | V4A, Q5-9 |
| Current Electrodes, 54 & 56 | J2 |
| Gating Circuit, 58 | U4C |
| Frequency Divider, 60 | U1 |
| LED Driver, 62 | Q1 |
| Attenuator, 64 | Q3, VR1 |
| Feedback Monitor LED Flasher, 66 | V5 (vco) |

Figure 4:
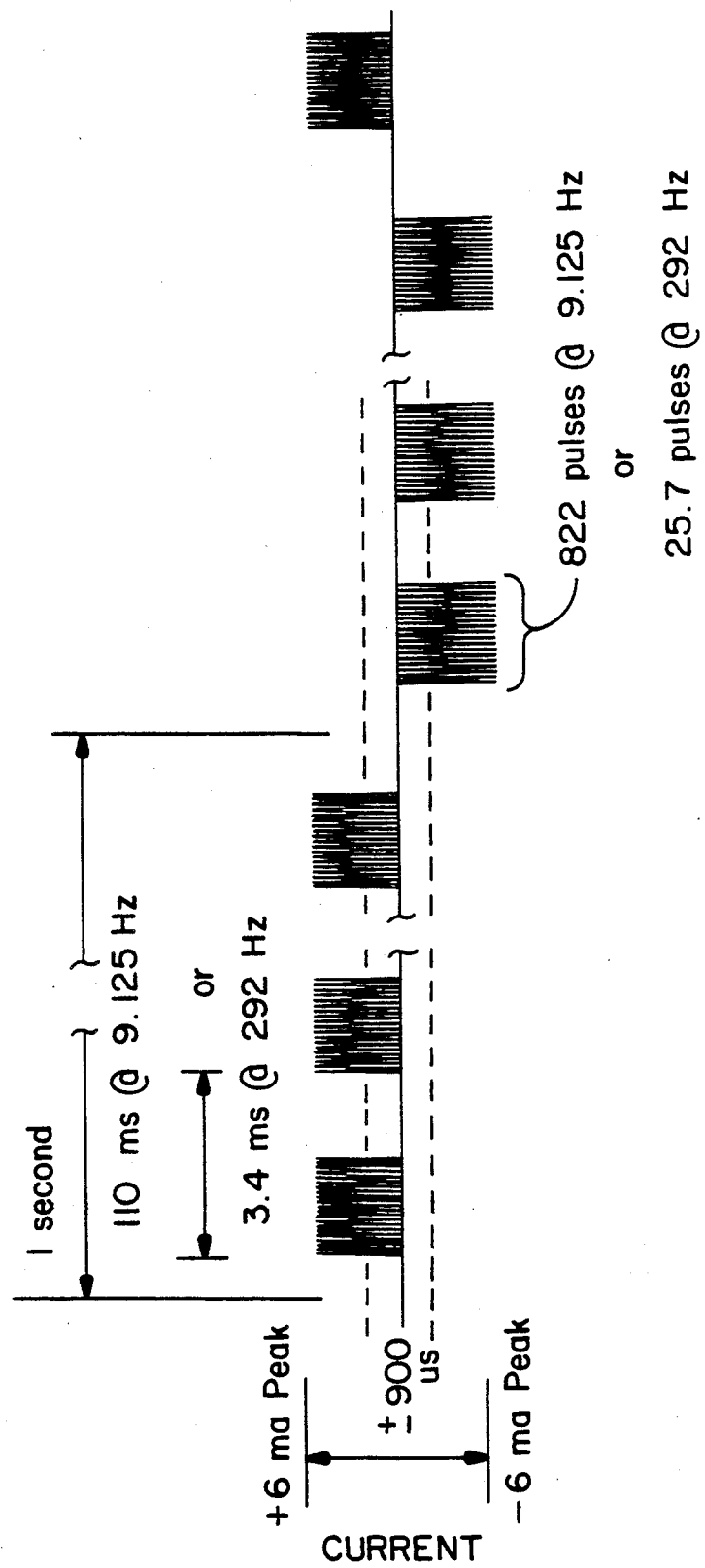
FIG. 4 is a simplified illustration of the essential features of the unique wave form of the electrical signal employed according to the present invention.

FIG. 4 illustrates the essential features of the unique wave form of the electrical signal employed in the improved TENS according to the present invention. As illustrated the vertical axis is D.C. current wherein the center line represents ground and the displacement upwards represents one polarity and displacement downward represents the inverse or reverse polarity at the pair of conductive electrodes. The horizontal axis is time. As seen in FIG. 4, the instantaneous current at maximum power is plotted as a function of time with insufficient resolution to perceive the carrier frequency (i.e., typically 15,000 Hz). What can be clearly seen is the inversion or more specifically the reversing of polarity at the electrode approximately every second in this specific illustration. Also, the monophasic character of the D.C. carrier signal is evident in that during any given one second burst of the 15,000 Hz carrier signal, current flows in only one direction (i.e., amplitude either above or below the center ground but not both). The on/off time modulation of the carrier signal at 9.125 Hz is suggested in that a sequence of 110 millisecond bursts chops the one second interval into approximately 9 cycles with approximately 50% duty cycle (i.e., current transmission during half of the cycle). In the case of 292 Hz a 3.4 millisecond burst chops the one second into 292 cycles. As further suggested in the first reversed polarity modulation cycle a burst of the 15,000 Hz carrier frequency would represent some 822 individual pulses within a given duty cycle at 9.125 Hz or 25.7 individual pulses, at 292 Hz. As further suggested in FIG. 4, the normal treatment range is confined to a current of up to about 900 microamps which is represented in the drawing as a central band well below the maximum current amplitude of 6 milliamps. It should be appreciated that the illustration of FIGS. 4 and 5 are not to scale and will vary depending on the selection and rate of polarity reversal at the electrodes.

Figure 5B:
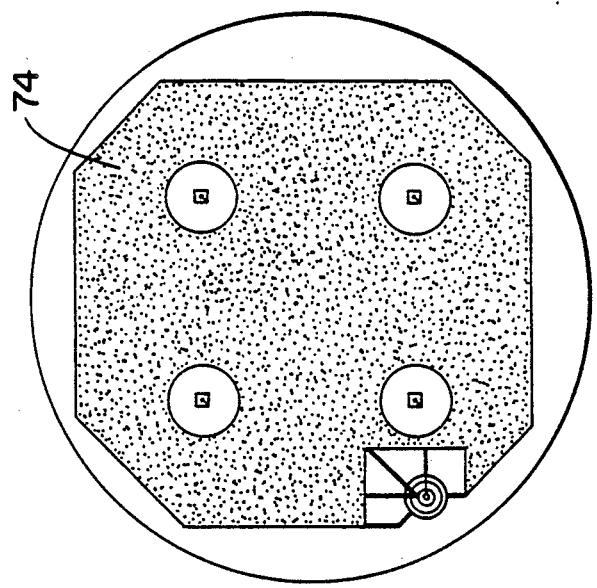
FIGS. 5a and 5b illustrate the circuitry associated with the novel LED/current electrode according to the present invention.
Figure 5A:
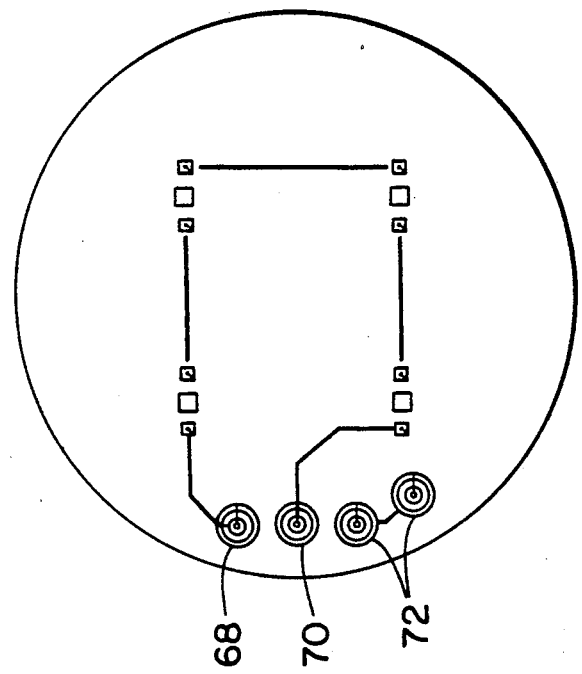

FIGS. 5a and 5b illustrate the printed circuit associated with the novel combined LED/current electrode according to the present invention. As illustrated in FIG. 5a, the back side of the printed circuit involves leads 68 and 70 which connect fours LED's (not shown) in series. The other leads 72 supply current to the tissue contacting current electrode 74 of FIG. 5b. Current electrode 74 is provided with four openings for insertion of the LED's into the light emitting circuitry 68 and 70. This circuit board is then incorporated into an appropriate housing as illustrated in FIG. 1.

The advantages of the improved TENS unit according to the present invention are viewed as being numerous and significant. The fact that the unit is a microcurrent TENS powered by a single 9 volt battery means the unit is highly portable, readily serviceable and safe under all normal operating conditions. The fact that the polarity at the electrodes is systematically reversed reduces the likelihood of any detrimental tissue damage in the vicinity of the electrodes. In this regard reversal of polarity every 0.05 seconds up to about 10 seconds (preferably from about 0.1 seconds to 8 seconds and most preferably about every second) is useful for purposes of this invention but other periodical reversal schemes including asynchronous, random and-or time delayed or interruption of the carrier signal should be considered equivalent. The unique wave profile results in extremely fast management of pain under treatment conditions that are virtually undetectable to the user. And, the overall therapeutic procedure is highly compatible with simultaneous treatment using IR and near IR pulsed therapy again accelerating the process of pain management.

Having thus described and exemplified the preferred embodiments with a certain degree of particularity, it is to be understood that the invention is not to be limited to the embodiments set forth herein for purposes of exemplification, but is to be limited only by the scope of the attached claims, including a full range of equivalents to which each element thereof is entitled.

I claim:

1. A microcurrent transcutaneous electrical nerve stimulator comprising:
   (a) a pair of electrode means for making surface contact and supplying electrical current to mammalian tissue; and
   (b) an electrical circuit means for supplying to said pair of electrode means from about 25 microamps up to about 900 microamps of a monophasic sequence of bursts of a D.C. carrier signal selected from the frequency range of at least 10,000 Hz to about 19,000 Hz which is modulated on and off in time at a frequency selected from the range of about 0.3 Hz up to 10,000 Hz and said bursts are characterized as having a periodicity greater in duration than that associated with the modulation frequency.

2. A microcurrent transcutaneous electrical nerve stimulator device of claim 1 further comprising a means for reversing electrode polarity wherein said sequential bursts are alternately inverted by reversing electrode polarity.

3. A microcurrent TENS device of claim 2 wherein reversal of polarity occurs from about every 0.05 seconds up to about every 10 seconds.

4. A microcurrent TENS device of claim 1 further comprising a means for adjusting the frequency of said D.C. carrier signals and a means for manually selecting the frequency of modulation from the group consisting of 9.125, 18.25, 73, 146, 292, 584, 1168, 2336 and 4672 Hz.

5. A microcurrent TENS device of claim 4 further comprising a means for reversing electrode polarity wherein said sequential bursts are alternately inverted by reversing electrode polarity from about every 0.05 seconds up to about every 10 seconds.

6. A microcurrent TENS device of claim 2 wherein the frequency of said D.C. carrier signal is about 15,000 Hz, the frequency of modulation is selected from the group consisting of 9.125 Hz and 292 Hz and said sequential bursts are inverted by reversing the polarity about every second.

7. A therapeutic electronic apparatus comprising:
(a) a pair of electrodes;
(b) an electrical circuit attached to said pair of electrodes further comprising;
  (i) a battery;
  (ii) means for producing a monophasic carrier signal selected from the frequency range of at least 10,000 Hz to 19,000 Hz,
  (iii) means for modulating the monophasic carrier signal on and off in time at a frequency selected from the range of about 0.3 Hz up to 10,000 Hz, and
  (iv) means for adjusting the current of said modulated monophasic carrier signal from about 25 microamps up to about 900 microamps; and
(c) an electronic circuit with means for inverting said modulated monophasic carrier signal by reversing electrode polarity with a periodicity greater in duration than that associated with the modulation frequency.

8. A therapeutic electronic apparatus of claim 7 wherein the carrier frequency is about 15,000 Hz, the modulating frequency is selected from the group consisting of 9.125, 18.25, 73, 146, 292, 584, 1168, 2336, and 4672 Hz and the periodicity for inverting by reversing the polarity is from about every 0.05 seconds up to about every 10 seconds.

9. A therapeutic electronic apparatus of claim 8 wherein the modulating frequency is either 9.125 Hz or 292 Hz.

10. A method of alleviating pain comprising the steps of:
(a) attaching a pair of electrodes to tissue in the proximity of the pain; and
(b) supplying across said pair of electrodes from about 25 microamps up to about 900 microamps of a monophasic sequence of bursts of a D.C. carrier signal selected from the frequency range of a least 10,000 Hz to about 19,000 Hz wherein said D.C. carrier signal is modulated on and off in time at a frequency selected from the range of about 0.3 Hz up to 10,000 Hz and wherein the polarity of the D.C. carrier signal is reversed at the electrodes between bursts with a periodicity greater in duration than that associated with the modulation frequency.

11. A method of claim 10 wherein the carrier frequency is about 15,000 Hz, the modulation frequency is selected from either 9.125 Hz or 292 Hz and the periodicity of reversing polarity is from about every 0.05 seconds up to about every 10 seconds.

12. A method of claim 10 wherein the carrier frequency is about 15,000 Hz, the periodicity of reversing polarity is about 0.05 seconds to about every 10 seconds and the modulation frequency is initially 9.125 Hz followed by a modulation frequency of 292 Hz.

13. A microcurrent transcutaneous electrical nerve stimulator device of claim 1 wherein at least one of said pair of electrode means further comprises at least one LED light source for making surface contact and supplying light to mammalian tissue and wherein said electrical circuit means further comprises circuit means for supplying electrical current to said LED light source such as to provide light synchronously with the electrical signal supplied to said pair of electrical current electrode means.

14. A therapeutic electronic apparatus comprising:
(a) a pair of electrodes;
(b) an electrical circuit attached to said pair of electrodes further comprising;
  (i) a battery;
  (ii) means for producing a monophasic carrier signal selected from the frequency range of at least 10,000 Hz to 19,000 Hz,
  (iii) means for modulating the monophasic carrier signal on and off in time at a frequency selected from the range of about 0.3 Hz up to 10,000 Hz, and
  (iv) means for adjusting the current of said modulated monophasic carrier signal from about 25 microamps up to about 900 microamps; and
wherein at least one of said pair of electrodes further comprises at least one LED light source also attached to said electrical circuit wherein said electrical circuit means further comprises circuit means for supplying electrical current to said LED light source such as to provide light synchronously with the electrical signal supplied to said pair of electrical current electrode means.

15. An improved transcutaneous electrical nerve stimulation electrode system comprising:
(a) a pair of electrode means wherein each of said electrode means are for making separate surface contact with mammalian tissue and for supplying a therapeutically stimulating electrical current to said mammalian tissue; and
(b) at least one LED light source means for making surface contact and for supplying light to mammalian tissue at the location of and synchronously with at least one of said pair of electrical current electrode means.

* * * * *